United States Patent [19]
Darlington et al.

[11] Patent Number: 5,600,729
[45] Date of Patent: Feb. 4, 1997

[54] EAR DEFENDERS EMPLOYING ACTIVE NOISE CONTROL

[75] Inventors: Paul Darlington; Gerald A. Powell, both of Southampton, United Kingdom

[73] Assignee: The Secretary of State for Defence in Her Britannic Majesty's Government of the United Kingdom of Great Britain and Northern Ireland, Hants, United Kingdom

[21] Appl. No.: 495,661

[22] PCT Filed: Jan. 26, 1994

[86] PCT No.: PCT/GB94/00151

§ 371 Date: Aug. 22, 1995

§ 102(e) Date: Aug. 22, 1995

[87] PCT Pub. No.: WO94/17512

PCT Pub. Date: Aug. 4, 1994

[30] Foreign Application Priority Data

Jan. 28, 1993 [GB] United Kingdom ............... 9301659

[51] Int. Cl.[6] ................................................ G10K 11/16
[52] U.S. Cl. ................................. 381/71; 381/72
[58] Field of Search ..................... 381/71, 72, 74, 381/25

[56] References Cited

U.S. PATENT DOCUMENTS

| | | | |
|---|---|---|---|
| 4,566,118 | 1/1986 | Chaplin et al. | |
| 4,985,925 | 1/1991 | Langberg et al. | 381/72 |
| 5,138,664 | 8/1992 | Kimura et al. | 381/72 |
| 5,172,416 | 12/1992 | Allie et al. | 381/72 |
| 5,251,263 | 10/1993 | Andrea et al. | 381/72 |
| 5,267,321 | 11/1993 | Langberg | 381/72 |
| 5,305,387 | 4/1994 | Sapiejewski | 381/72 |

FOREIGN PATENT DOCUMENTS

WO91/13429  9/1991  WIPO.

*Primary Examiner*—Forester W. Isen
*Attorney, Agent, or Firm*—Nixon & Vanderhye P.C.

[57] ABSTRACT

An ear defender having one or more microphones (1) for detecting the sound level in the proximity of the wearer's ear, one or more speakers (4) for generating a noise reduction signal within the earshell, and a digital feedback controller (W) for generating a feedback signal derived from the output of the microphones and for applying said feedback signal to the speaker inputs, and estimation means (F') for providing an estimation of the earshell transfer function and subtracting from the input to the feedback controller a signal representing the estimated electroacoustic transfer function of the system. The operation of the digital feedback controller may be controllable by the output of a computational circuit (C) operable on the difference between the microphone output and the feedback controller input modified by a model (F") of the electroacoustic transfer function. A second, analogue or digital, feedback controller (W') may be included to provide an approximate feedback signal to the speakers and to improve the impulse response of the system.

10 Claims, 4 Drawing Sheets

EAR DEFENDERS EMPLOYING ACTIVE NOISE CONTROL

This invention relates to noise reduction techniques, and in particular to the application of Active Noise Reduction (ANR) in ear defenders.

The application has application to ear defenders of the type required simply to reduce the ambient level of noise to enable the wearer to concentrate better on his task or to reduce or avoid physical or psychological damage caused by an excessive noisy environment, as well as to ear defenders incorporating means for communicating audible data (such as speech or warning signals) to the wearer. In the latter case, the invention is intended to provide means for attenuating ambient noise while leaving the data signal unaffected.

Conventional ear defenders of the type at present contained in the helmets of aircrew can only provide a certain amount of noise protection for the wearer. The amount of protection provided by these conventional, passive means is primarily dictated by the mass, volume and seal stiffness of the hearing defender and the spectral characteristics of the noise field. Thee is a requirement to provide greater hearing protection (with little or no increase in helmet mass) and this requirement will grow as new aircraft with more demanding noise fields come into service, and it will become ever more desirable to provide means for adapting the noise reduction action of the defender to changes in the cavity configuration caused by its movement over the wearer's head or high "G" forces.

ANR has been successfully demonstrated in the past and a basic analogue technique is described in UK patent application no 2188210A. This technique is based upon a conventional circumaural ear defender and means are provided for sensing the noise field at the wearer's ear using a miniature microphone. The information from the microphone is then processed and used to generate, via a speaker inside the ear defender, an acoustic field which is in anti-phase with respect to the noise at the wearer's ear. The effect is to acoustically cancel some of the noise reaching the wearer's ear and thus provide noise reduction which is additional to that provided by the passive defender.

Present, conventional ANR systems are implemented using an analogue control strategy.

FIG. 1 illustrates the overall system, in which the output from a miniature microphone 1 located close to the wearer's ear 2 is applied to a feedback controller 3. The output of the feedback controller is added to the input signal (when present) to a speaker 4 to increase the stability of the system and to reduce noise enhancement in certain frequency bands. Because the controller 3 employs an analogue filter, the filter is fixed and therefore retains the same characteristics over time. Since the same filter is used in all implementations, the filter's characteristics in both amplitude and phase are arranged to be approximations of the average requirements.

In the illustration, the microphone and speaker are depicted as single components. In practice, a number of separate microphones or speakers may be deployed within the earshell and may be weighted and distributed in any required manner.

FIG. 2 shows the system applied to a simple ear defender and reduced to a block diagram.

Referring to FIG. 2, Vm is the voltage at the output terminals of the sense microphone and the two inputs to the summation point are the noise at the microphone's diaphragm and the ANR signal arriving at the microphone's diaphragm. The block F represents the operator relating the input to the speaker 4 to the corresponding output of the microphone 1 and is governed by the electrical transfer functions of the speaker and microphone and the acoustic transfer function of the earshell itself. This operator will be referred to hereinafter as the electroacoustic transfer function of the system.

The block W represents an electronic controller whose task it is to operate on the microphone voltage and produce a signal which, when operated on by the aforementioned electroacoustic transfer function, will result in a reduction of acoustic noise at the microphone. Note that $$Vm = Noise + Vm.W.F$$

and therefore $$Vm/Noise = 1/(1-W.F)$$

Because of the nature of the variables, W.F can for certain values equal unity and since the system can therefore under certain conditions have a Vm/Noise of infinity, ie it can become unstable.

This invention consists of an ear defender comprising an earshell, detector means for detecting the sound level in the proximity of the wearer's ear, output means for generating a noise reduction signal within the earshell, and a digital feedback controller for generating a feedback signal derived from the output of said detector means and for applying said feedback signal to the input of the output means, characterised by estimation means for providing an estimation of the earshell transfer function and subtracting from the input to the feedback controller a signal representing the estimated electroacoustic transfer function of the system, and a second feedback controller for providing active noise control on the basis of an average configuration for the system.

By way of example, a number of embodiments of the invention will now be described with reference to the schematic block circuit diagrams shown in FIGS. 3 to 7 of the drawings, of which FIG. 3 illustrates a system similar to that shown in FIG. 2 but having a digital controller and a "feed-forward" loop intended to overcome the instability of the conventional arrangements described above;

Figure 1:
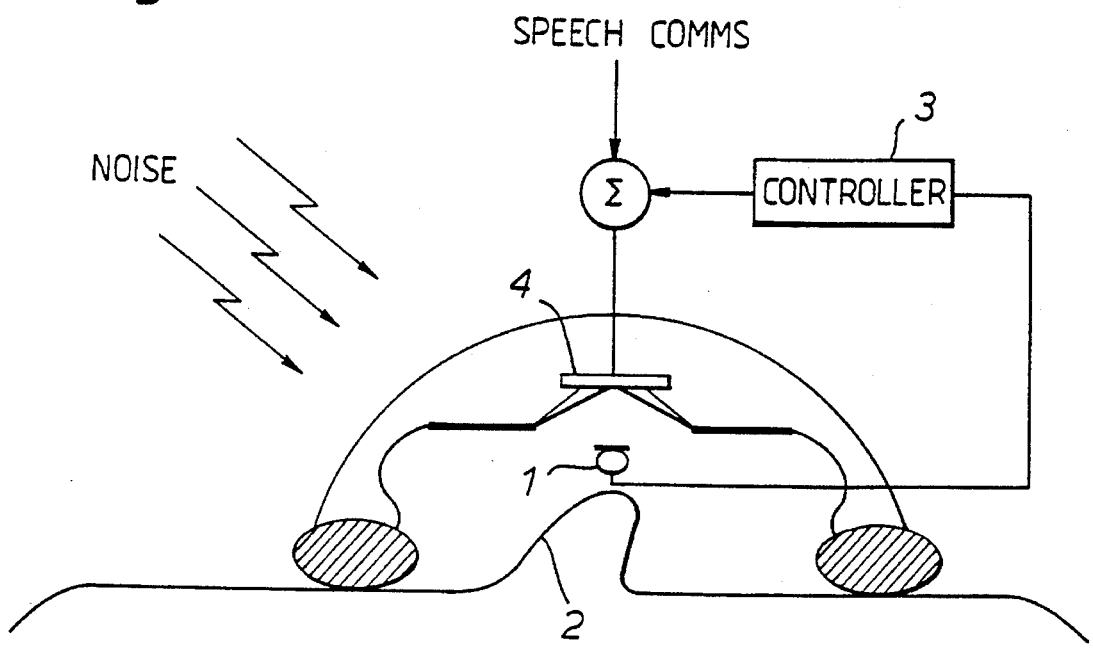

The feedback system described above with reference to FIGS. 1 and 2 may be implemented in digital form having a behaviour similar to that of the analogue system. This means that the transfer function between the voltage at the sense microphone and noise input has poles and thus, as with the analogue system, the digital system can under certain conditions become unstable.

Figure 3:
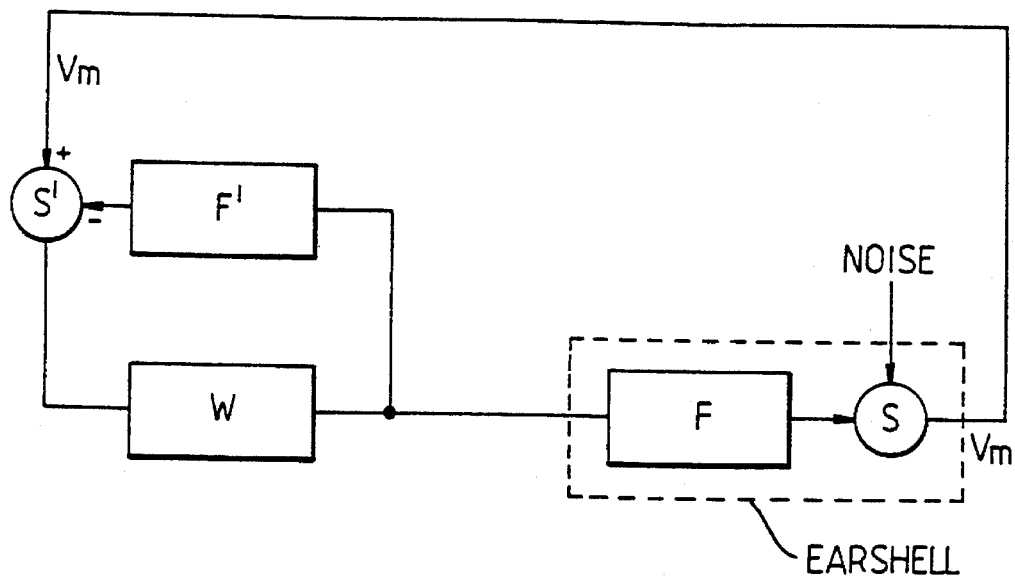

The purpose of the system shown in FIG. 3 is to make the system acoustically stable by removing from the feedback loop the effects of the forward electroacoustic transfer function of the hearing defender, microphone and speaker combination. This is achieved by employing a model of the function and subtracting its output from the output S of the microphone.

Figure 2:
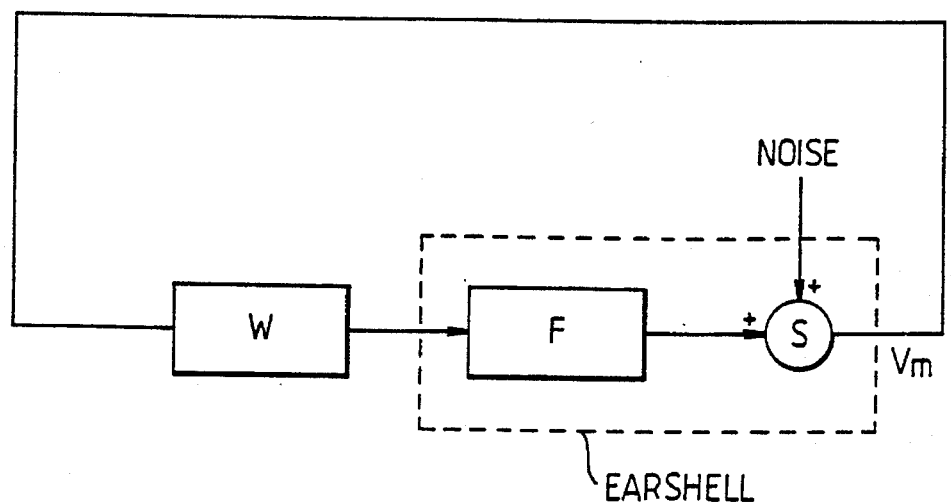

This system is identical to that shown in FIG. 2, except that a component marked F' has been added between the input to the transfer function F (essentially the input line to the speaker 4 of FIG. 1 ) to a summation point S' in the feedback line, ie the input line to the digital controller W. The component F' generates an estimation or approximation of the electroacoustic transfer function F and its purpose is to present to the summation point S' a signal which is identical to that being fed back from the output of the (noise free) electroacoustic transfer function.

This signal is then subtracted from the actual feedback signal and thus the regenerative effects of the feedback system are removed. This results in an overall system transfer function with no poles, and which is therefore inherently stable. The required characteristics of F' may be determined by automatically measuring the electroacoustic transfer function at 'power up' or 'turn on' time.

From FIG. 3, note that $$Vm = Noise + Noise \cdot W.F$$

or $$Vm/Noise = 1 + W.F$$

So, for any value of W.F, the value of Vm/noise is always finite. Thus instability cannot occur (since the transfer function has only zeros, no poles).

Figure 4:
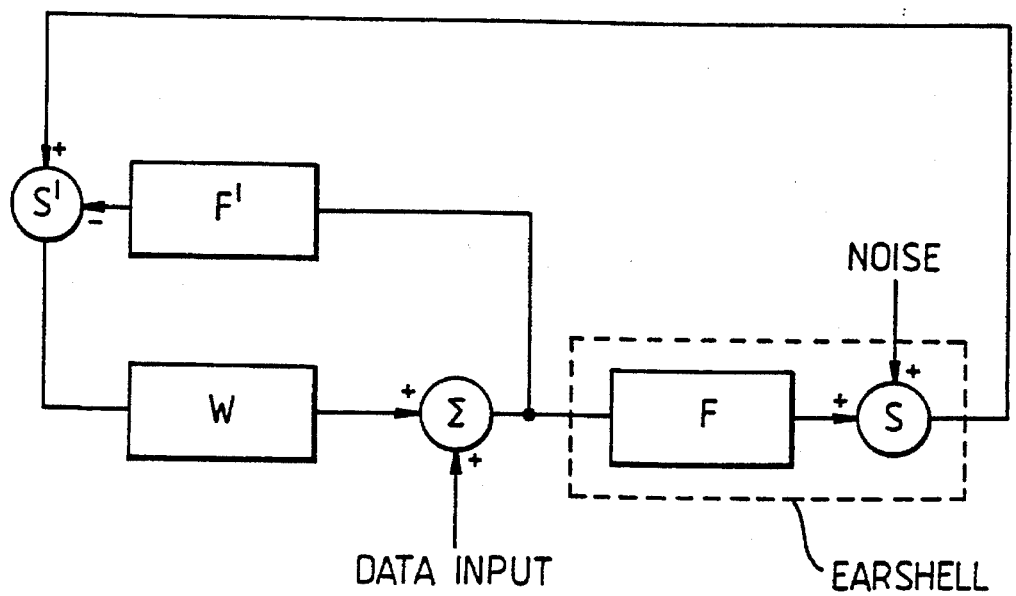
FIG. 4 illustrates a similar system but possessing an input for speech or other data.

FIG. 4 illustrates a similar system but with the addition of a data input, as required in a practical communications headset. The data is added before the point at which the model's input is derived (ie at the input to the speaker), and the transfer function is unchanged so that there is no need for pre- compensation of the data sisal, as is required in the present implementation of analogue ANR systems.

Figure 5:
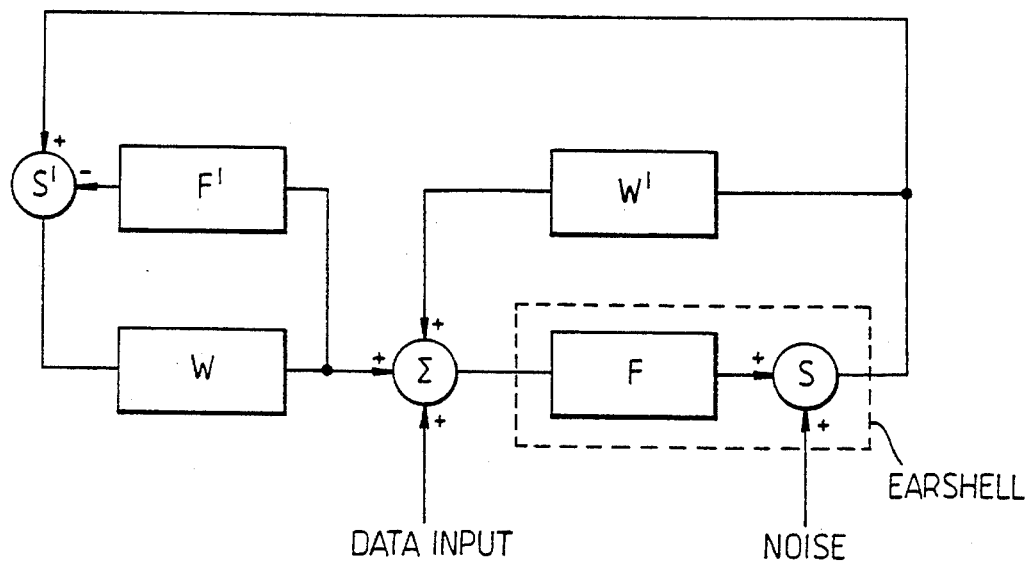
FIG. 5 illustrates a similar system but including an additional, analogue controller for reducing the computational demand on the digital controller.

In the embodiment shown in FIG. 5, a system similar to that shown in FIGS. 3 or 4 is modified by the introduction of an additional component W' which consists of an analogue ANR controller. All other aspects of the system operation are as described in the preceding paragraphs with the obvious exception that the system which is to be controlled by the digital controller W now has an analogue controller "inside" it.

The analogue controller W' is an approximation of the average controller required to achieve active noise reduction over all cases of fit, noise etc (as in the analogue-only case). The feed-forward digital controller W is the digital feedback cancelling controller and its transfer function must reflect the presence of the analogue controller W' in the system it is trying to control. The effect of the inclusion of the analogue system is to alter the dynamics of the system by shortening the impulse response of the electroacoustic transfer function and enable the digital controller to exert more control over the system.

The effect of including the analogue feedback loop around the earshell is to reduce the length (in time) of the impulse response of the electro-acoustic system. This makes the model of the forward transfer function simpler to measure and implement in the feed-forward element of the system. It is worth noting that this system is not merely the obvious combination of two techniques in order to gain the sum of the benefits from each. There is a degree of synergy involved in that the analogue feedback system is employed in order to alter the dynamic characteristics of the system to be controlled such that the task of the digital feed-forward controller is made simpler, and therefore cheaper, to implement.

Because the hybrid system just described incorporates a feedback controller in the system, there are poles in the transfer function. However, since the feedback ANR is not being used to achieve high levels of active noise reduction, a high stability margin (low controller gain) can be employed thus ensuring stability. The high performance ANR is achieved by using the feed-forward part of the system, which is inherently stable.

In practice, the electroacoustic transfer function of the earshell is continually changing and in order to maintain optimal ANR conditions the controller is required to reflect these changes. This is achieved in the embodiment of the invention illustrated in FIG. 6, in which the digital feed-forward controller is adaptive, in contrast with the fixed controller in the feed-forward systems outlined hitherto.

An embodiment having this feature has particular application in hearing defenders for wearers liable undergo rapid movements or high "G" forces, such as fast-jet pilots. Became the electroacoustic forward transfer function of the earshell assembly changes due to fit and aircraft movement etc, a controller which adapts in real time in order to accommodate these changes will deliver obvious performance benefits.

Figure 6:
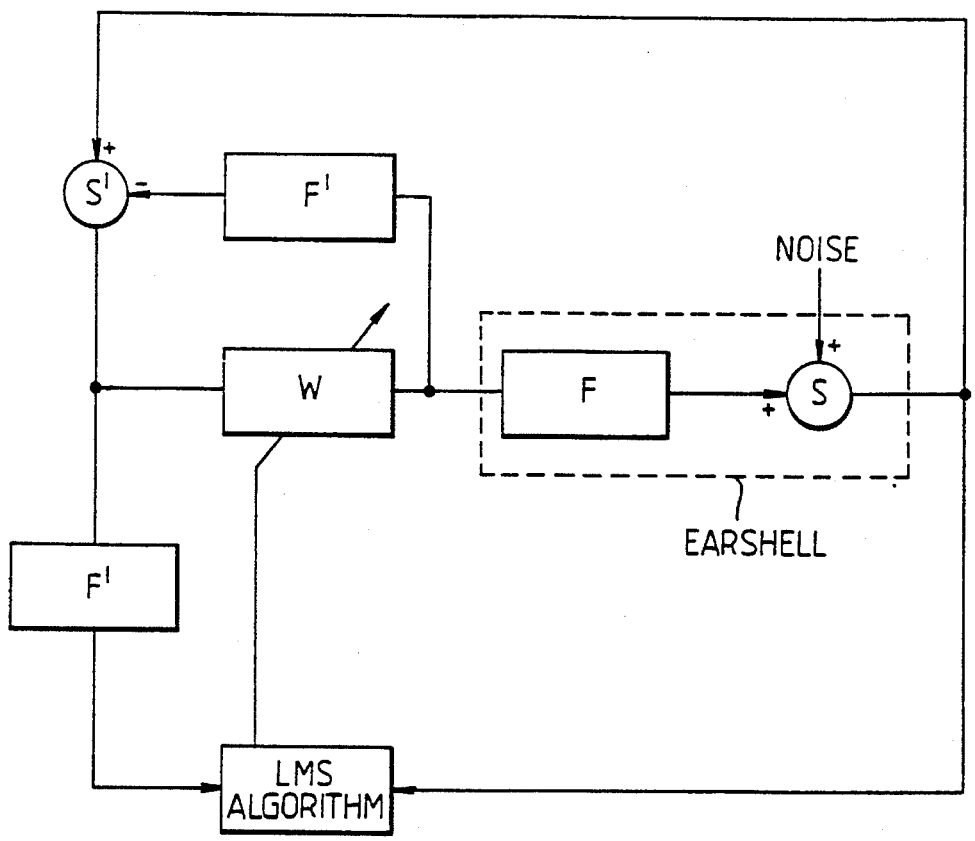
FIG. 6 illustrates a system similar to that shown in FIG. 3 in which the digital controller is variable and controlled by information derived from the current electro-acoustic properties of the headshell.

Comparing the embodiment illustrated in FIG. 6 with the FIG. 3 embodiment, the controller W is variable (or adaptive) and is modified by a computational circuit C the output of which is the operation of the well-known LMS algorithm on the difference between the output of the electroacoustic system and the input to the controller W as modified by an additional controller F".

The controller F" embodies an estimate of the forward electroacoustic transfer function and is included to compensate for the fact that the electroacoustic system is actually in the control loop of the adaptive system. The circuit C is arranged to calculate the values of the coefficients required to implement the adaptive controller W.

As with the system shown in FIGS. 4 and 5, it is possible to reduce the demand placed on the controller W by modifying the feedback loop by means of an analogue controller W'. Such a system is illustrated by FIG. 7.

Figure 7:
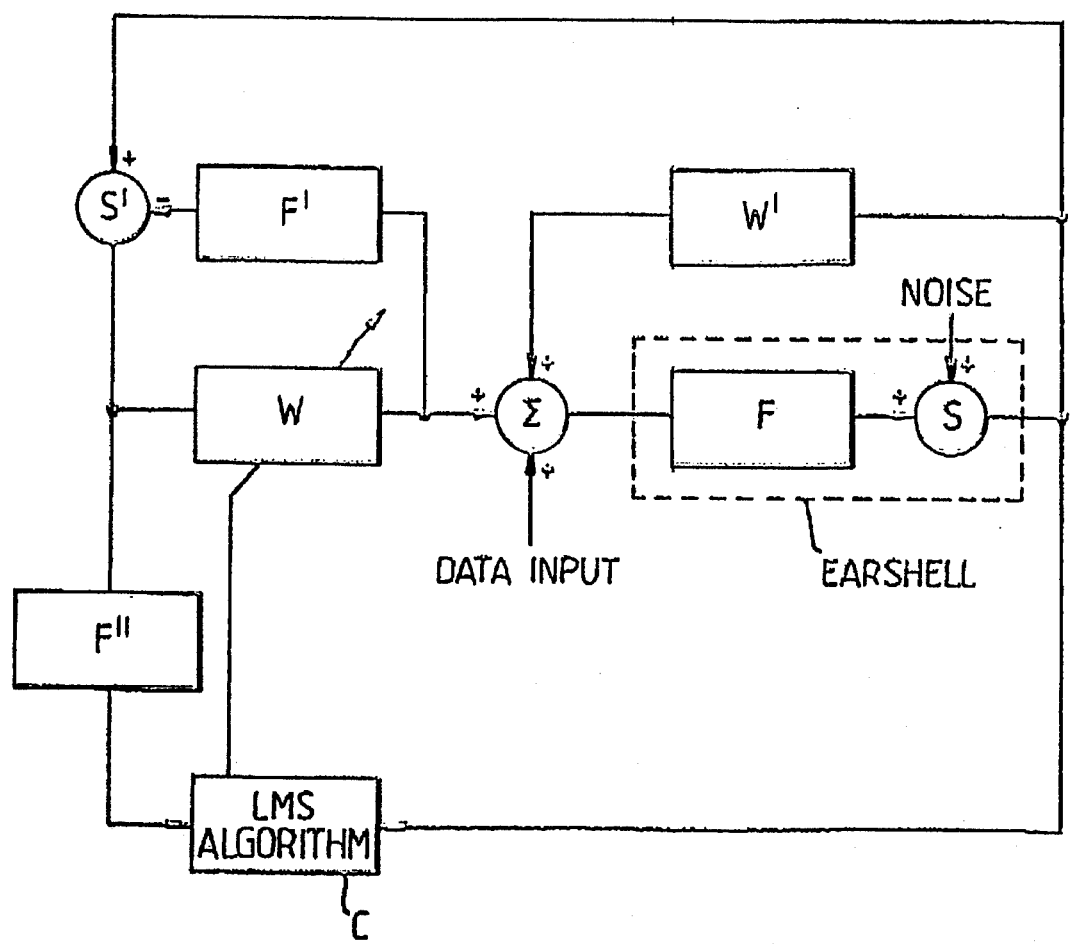
FIG. 7 illustrates the application of the particular design features shown in FIG. 6 to the hybrid system shown in FIG. 5.

The system shown in FIG. 7 is identical to that shown in FIG. 6 except that an analogue controller W' is incorporated in the electroacoustic assembly. This yields the same type of performance benefit as described with reference to FIG. 4, ie the analogue ANR system effectively shortens the impulse response of electroacoustic system which means that the task, and hance the logic, of the digital feed-forward system is simplified. Conversely, it can be said that the inclusion of the analogue ANR system means that more complex electroacoustic systems can be controlled (with a given amount of computational capacity in the digital feed-forward controller).

The use of digital techniques for the systems illustrated in FIGS. 3 to 7 make it a relatively straightforward matter to use more than one sensing microphone, and more than one speaker component. In practice, the signals or outputs from these must be "intelligently" weighted in any required manner and for practical purposes such weighting is only possible with the use of digital techniques.

Two general points should be made with reference to the digital ANR systems described. Firstly, all of the systems described are capable of dealing with broad band noise. Secondly, the adaptive systems described are capable of exploiting a trigger signal (from an external source which is related to the noise) in order to effect high degrees of reduction of that noise. This property of adaptive systems makes them particularly useful for situations where periodic noise is prevalent but does not restrict their use to the periodic noise situation.

We claim:

1. An ear defender comprising an earshell, detector means (1) for detecting the sound level in the proximity of the wearer's ear, output means (4) for generating a noise reduction signal wig the earshell, and a digital feedback controller (W) for generating a feedback signal derived from the output of said detector means and for applying said feedback signal to the input of the output means, characterised by estimation means (F') for providing an estimation of the earshell transfer function and subtracting from the input to the feedback controller a signal representing the estimated electroacoustic transfer function of the system, and a second feedback controller (W') for providing active noise control on the basis of an average configuration for the system.

2. An ear defender according to claim 1 including means for determining the configuration and operation of the feedback controller (W) and the estimation means (F') when the system is activated or on other known occasions.

3. An ear defender according to claim 1 in which the second feedback controller (W) operates by analogue means.

4. An ear defender according to claim 1 including means for modifying the action of the first feedback controller (W) to reflect variations in the electroacoustic transfer function of the earshell.

5. An ear defender according to claim 4 in which the means for modifying the action of the first feedback controller (W) comprises a computational circuit operating on the difference between the output of the detector means and the output of an additional controller (F") which consists of the sum of a model of the electroacoustic transfer function and the input of the fast feedback controller.

6. An ear defender according to claim 5 in which the computational circuit operates on the said difference by means of an LMS algorithm.

7. An ear defender according to claim 1 in which the detector means comprise one or more microphones.

8. An ear defender according to claim 1 in which the output means for generating a noise reduction signal comprise one or more loudspeakers.

9. An ear defender according to claim 1 including means for communicating aural information to the wearer, said means being applied to the input of the output means for generating a noise reduction signal.

10. An ear defender according to claim 1 including means for controlling the operation of the fast feedback controller and the estimating means in accordance with the nature of the ambient noise.

* * * * *